United States Patent [19]
Dauth et al.

[11] Patent Number: 5,523,436
[45] Date of Patent: Jun. 4, 1996

[54] CATALYSTS FOR HYDROSILYLATION REACTIONS

[75] Inventors: Jochen Dauth; Udo Peetz; Bernward Deubzer, all of Burghausen, Germany

[73] Assignee: Wacker-Chemie GmbH, Munich, Germany

[21] Appl. No.: 165,136

[22] Filed: Dec. 10, 1993

[30] Foreign Application Priority Data

Dec. 16, 1992 [DE] Germany .................. 42 42 469

[51] Int. Cl.$^6$ .................. C07F 7/08; C07F 15/00
[52] U.S. Cl. .................. 556/12; 556/9; 556/22; 556/26; 556/136; 556/137; 556/479; 526/93; 528/15; 546/2
[58] Field of Search .................. 556/22, 9, 26, 556/12, 136, 137, 479; 528/15; 526/93; 546/2

[56] References Cited

U.S. PATENT DOCUMENTS

| | | |
|---|---|---|
| 2,476,166 | 7/1949 | Wayo . |
| 2,823,218 | 2/1958 | Speier . |
| 3,445,420 | 5/1969 | Kookootsedes . |
| 3,814,730 | 6/1974 | Karstedt . |
| 4,302,401 | 11/1981 | Oswald .................. 556/22 |
| 4,473,505 | 9/1984 | Mitchell .................. 556/22 X |
| 4,504,645 | 3/1985 | Melancon . |
| 4,620,021 | 10/1986 | Starzewski et al. .................. 556/22 X |

OTHER PUBLICATIONS

Chemical Abstracts, vol. 111, 1989, abstract No. 23725q.
Chemical Abstracts, vol. 112, 1990, abstract No. 200382u.
Chemical Abstracts vol. 102, 1985, abstract No. 46319p.
Journal of Organometallic Chemistry, vol. 139 (1977) pp. 349–354.
Chemical Abstracts, vol. 91, 1979, abstract No. 167611r.
Chemical Abstracts, vol. 83, 1975, abstract No. 70786y.
Chemical Abstracts, vol. 114, 1991, abstract No. 54746p.
Journal of Organometallic Chemistry, vol. 208, 1981, pp. C21–C24.
Chemical Abstracts, vol. 106, 1987, abstract No. 167625b.
Journal of Organometallic Chemistry, vol. 459, 1993, pp. 359–364.
D. S. Moore et al., Advances in Inorganic Chemistry and Radiochemistry vol. 30, pp.1–68, 1986.
M. Julliard et al., Synthesis, p. 49, 1982.
T. P. Ahern et al., Can J. Chem. 55, 1701 (1977) and M. A. Kelly et al., J. Chem. Soc., Perkin Trans. II, 1649 (1982).

*Primary Examiner*—Paul F. Shaver
*Attorney, Agent, or Firm*—Martin Connaughton

[57] ABSTRACT

Novel catalysts of the general formula $$MX_aY_b,$$

in which

M is Pt, Pd, Rh, Ru, Os or Ir,

X is a triazene, tetrazene, tetrazadiene or pentazadiene ligand,

Y is a ligand selected from Cl, Br, I, $NH_3$, $P(C_2H_5)_3$, $P(C_6H_5)_3$, H, CO, 1,5-cyclooctadiene, pyridine, bipyridine, acetate, acetylacetonate, phenylnitrile, ethylenediamine, acetonitrile, 2,5-norbornadiene, nitrate, nitrite, $H_2O$, benzene, diphenylphosphinoethane and 1,3-divinyl-1,1,3,3-tetramethyldisiloxane, a is 1, 2, 3 or 4 and b is 0 or an integer from 1 to 6, are described.

The catalysts promote the addition of Si-bonded hydrogen onto an aliphatic multiple bond, in which the catalysts are activated by heating at temperatures of 50° to 250° C., by irradiation with light, by addition of Brönsted acids and/or by addition of acid-forming agents.

The catalysts are used in addition crosslinking organopolysiloxane compositions and for the reaction of organosilicon compounds containing Si-bonded hydrogen atoms with organic compounds containing aliphatic multiple bonds.

5 Claims, No Drawings

CATALYSTS FOR HYDROSILYLATION REACTIONS

FIELD OF INVENTION

The invention relates to transition metal catalysts. The invention further relates to aryl-alkyltriazenido transition metal complexes and to processes for their preparation. The invention further relates to crosslinkable compositions and to a process for the reaction of organosilicon compounds containing Si-bonded hydrogen atoms with organic compounds containing aliphatic multiple bonds in the presence of catalysts.

BACKGROUND OF INVENTION

Triazenido, tetrazenido, tetrazadienido and pentazadienido transition metal complexes are known from D. S. Moore et al., Advances in Inorganic Chemistry and Radiochemistry, Volume 30, pages 1–68, 1986.

While diaryl-triazenido transition metal complexes are known, aryl-alkyl-triazenido transition metal complexes have not been described to date. Only a triazenido-platinum complex of the formula $PtZ_2(ArNNNMe)_2$ (Z=Cl or I; Ar=an aryl radical; Me=a methyl radical) having an antitumor activity is described in M. Julliard et al., Synthesis, page 49, 1982.

It is known that the addition of Si-bonded hydrogen onto an aliphatic multiple bond, which is often called hydrosilylation, can be promoted by catalysts, in particular platinum compounds. In this context, reference may be made to U.S. Pat. No. 3,814,730 (to General Electric Co., issued Jun. 4, 1974) and U.S. Pat. No. 2,823,218 (to Dow Corning, issued Feb. 11, 1958). These catalysts are distinguished by a low activation energy and must often be inhibited in addition-crosslinking systems.

SUMMARY OF INVENTION

The object of the invention was to provide catalysts which have a high activation energy and require no inhibition in addition-crosslinking systems, but, after activation, promote addition of Si-bonded hydrogen onto an aliphatic multiple bond. The object is achieved by the invention.

The invention relates to catalysts of the general formula $$MX_aY_b \qquad (I)$$

in which

M is Pt, Pd, Rh, Ru, Os or Ir,

X represents a triazene, tetrazene, tetrazadiene or pentazadiene ligand selected from the group consisting of; $ANNNR$, $ANNNRR^1$, $ANNNA^1$, $ANR^1NNNR^2A^1$, $ANNNNA^1$, $ANNNR^3NNA^1$ and $ANNNNNA^1$ in which R represents a monovalent, optionally substituted hydrocarbon radical having 1 to 18 carbon atoms per radical or a radical of the formula $-SiR^6_c(OR^6)_{3-c}$, $R^1$, $R^2$ and $R^3$ are identical or different and represent a hydrogen atom or a monovalent optionally substituted hydrocarbon radical having 1 to 18 carbon atoms per radical, and A and $A^1$ are identical or different and represent a radical of the formula

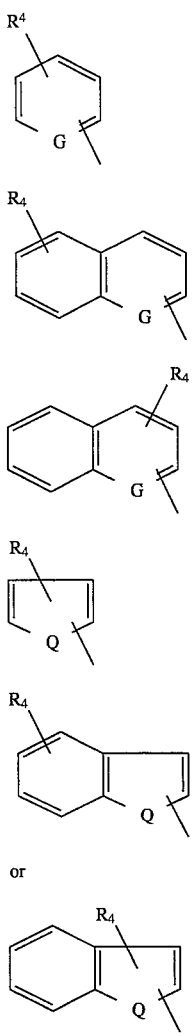

in which

G is CH or N and

Q is S, O or NH, $R^4$ represents a monovalent optionally substituted hydrocarbon radical having 1 to 12 carbon atoms per radical or a radical of the formula $-F$, $-Cl$, $-Br$, $-I$, $-H$, $-NH_2$, $-NR^6_2$, $-NO_2$, $-OH$, $-OR^6$, $-SH$, $-CN$, $-COOH$, $-COCl$, $-CONH_2$, $-COR^6$, $-CHO$, $-SO_2NHR^6$, $-SO_3H$, $-SO_2Cl$ or $-R^5-SiR^6_c(OR^6)_{3-c}$, $R^5$ represents a divalent hydrocarbon radical having 1 to 8 carbon atoms per radical, $R^6$ is identical or different and represents an alkyl radical having 1 to 8 carbon atoms per radical and c represents 0, 1, 2 or 3, Y is identical or different and represents a ligand selected from the group consisting of Cl, Br, I, $NH_3$, $P(C_2H_5)_3$, $P(C_6H_5)_3$, H, CO, 1,5-cyclooctadiene, pyridine, bipyridine, acetate, acetylacetonate, phenylnitrile, ethylenediamine, acetonitrile, 2,5-norbornadiene, nitrate, nitrite, $H_2O$, benzene, diphenylphosphinoethane and 1,3-vinyl-1,1,3,3-tetramethyldisiloxane, a represents 1, 2, 3 or 4 and b represents 0 or an integer from 1 to 6.

The invention further relates to transition metal complexes of the general formula $$M'X'_aY_b \qquad (II),$$

in which

M' is Pt, Pd, Rh and Ru,

X' represents a triazene ligand of the general formula ANNNR' in which

R' represents a monovalent, optionally substituted hydrocarbon radical having 1 to 18 carbon atoms per radical, excluding aromatic hydrocarbon radicals in which the aromatic part is bonded directly to the nitrogen atom, or a radical of the formula $-SiR^6{}_c(OR^6)_{3-c}$, and A, Y, a and b have the meaning given above for these symbols, with the proviso that platinum-triazenido complexes of the formula $PtZ_2[ANNN(CH_3)]_2$, are excluded in which Z represents Cl or I and A has the meaning given above for this symbol.

The invention furthermore relates to a process for the preparation of the transition metal complexes, which comprises reacting triazenes of the formula ANNNHR' in which A and R' have the meaning given above for these symbols, with transition metal compounds of the formula $M'Y_d$ in which M' and Y have the meaning given above for these symbols and d represents an integer from 1 to 8, in the presence of bases.

Triazenido complexes of transition metals, with the exception of the aryl-alkyl-triazenido complexes of transition metals, tetrazenido complexes of transition metals, tetrazadienido complexes of transition metals and pentazadienido complexes of transition metals and the structure thereof are described in the initially mentioned literature reference, D. S. Moore et al., Advances in Inorganic Chemistry and Radiochemistry, Volume 30, pages 1 to 68, 1986.

Examples of radicals R are alkyl radicals, such as the methyl, ethyl, n-propyl, iso-propyl, n-butyl, iso-butyl, tert-butyl, n-pentyl, iso-pentyl, neo-pentyl and tert-pentyl radical; hexyl radicals, such as the n-hexyl radical; heptyl radicals, such as the n-heptyl radical; octyl radicals, such as the n-octyl radical, and iso-octyl radicals, such as the 2,2,4-trimethylpentyl radical; nonyl radicals, such as the n-nonyl radical; decyl radicals, such as the n-decyl radical, and dodecyl radicals, such as the n-dodecyl radical; and octadecyl radicals, such as the n-octadecyl radical; cycloalkyl radicals, such as the cyclohexyl radical; alkenyl radicals, such as the vinyl, 1-propenyl, 1-butenyl, 2-butenyl, allyl, isobutenyl, 1-pentenyl and 2-methyl-1-butenyl radical; alkynyl radicals, such as the ethynyl, propargyl, 1-propynyl and 1-butynyl radical, and aralkyl radicals, such as the benzyl radical and the α- and β-phenylethyl radical; alkyl radicals are preferred.

Examples of substituted hydrocarbon radicals R are haloalkyl radicals, such as the 3,3,3-trifluoro-n-propyl radical, the 2,2,2,2',2',2'-hexafluoroisopropyl radical, the heptafluoroisopropyl radical, the 3-chloro-n-propyl radical, 2-ethyl bromide and 3-propyl bromide; hydroxyalkyl radicals, such as radicals of the formula $HOCH_2CH_2OCH_2CH_2-$, $HOCH_2CH_2-$ and $CH_3CH_2CH(OH)CH_2-$; aminoalkyl radicals, such as the aminomethyl and aminoethyl radical; carboxyalkyl radicals, such as radicals of the formula $-(CH_2)_7COOH$, $-(CH_2)_8COOH$ and $-CH_2COCH_2CH_2COOH$ and esters and amides thereof $-(CH_2)_7COOCH_3$, $-(CH_2)_7COOC_2H_5$, $-(CH_2)_7CONH_2$, $-(CH_2)_8COOCH_3$, $-(CH_2)_8COOC_2H_5$, $-(CH_2)_8CONH_2$, and a radical of the formula $-CH(COOC_2H_5)_2$; and substituted aralkyl radicals, such as the substituted benzyl radical and the substituted α- and β-phenylethyl radical.

Examples of hydrocarbon radical R and substituted hydrocarbon radicals R apply in their full scope to hydrocarbon radicals R' and substituted hydrocarbon radicals R'.

Examples of radicals $R^1$, $R^2$ and $R^3$ are alkyl radicals, such as the methyl, ethyl, n-propyl, iso-propyl, n-butyl, iso-butyl, tert-butyl, n-pentyl, iso-pentyl, neo-pentyl and tert-pentyl radical; hexyl radicals, such as the n-hexyl radical; heptyl radicals, such as the n-heptyl radical; octyl radicals, such as the n-octyl radical, and iso-octyl radicals, such as the 2,2,4-trimethylpentyl radical; nonyl radicals, such as the n-nonyl radical; decyl radicals, such as the n-decyl radical, and dodecyl radicals, such as the n-dodecyl radical; and octadecyl radicals, such as the n-octadecyl radical; cycloalkyl radicals, such as the cyclohexyl radical; alkenyl radicals, such as the vinyl, 1-propenyl, 1-butenyl, 2-butenyl, allyl, isobutenyl, 1-pentenyl and 2-methyl-1-butenyl radical; alkynyl radicals, such as the ethynyl, propargyl, 1-propynyl and 1-butynyl radical, aryl radicals, such as the phenyl radical; alkaryl radicals, such as the o-, m- and p-tolyl radical and the p-ethylphenyl, p-butylphenyl and p-hexylphenyl radical; and aralkyl radicals, such as the benzyl radical and the α- and β-phenylethyl radical.

Examples of substituted hydrocarbon radicals $R^1$, $R^2$ and $R^3$ are haloalkyl radicals, such as the 3,3,3-trifluoro-n-propyl radical, the 2,2,2,2', 2', 2'-hexafluoroisopropyl radical, the heptafluoroisopropyl radical, the 3-chloro-n-propyl radical, 2-ethyl bromide and 3-propyl bromide; haloaryl radicals, such as the o-, m- and p-chlorophenyl radical and the o-, m- and p-bromophenyl radical; substituted aryl radicals, such as the 4-cyanophenyl, 4-nitrophenyl and 4-methoxyphenyl radical; hydroxyalkyl radicals, such as radicals of the formula $HOCH_2CH_2OCH_2CH_2-$, $HOCH_2CH_2-$ and $CH_3CH_2CH(OH)CH_2-$; aminoalkyl radicals, such as the aminomethyl and aminoethyl radical; carboxyalkyl radicals, such as radicals of the formula $-(CH_2)_7COOH$, $-(CH_2)_8COOH$ and $-CH_2COCH_2CH_2COOH$ and esters and amides thereof $-(CH_2)_7COOCH_3$, $-(CH_2)_7COOC_2H_5$, $-(CH_2)_7CONH_2$, $-(CH_2)_8COOCH_3$, $-(CH_2)_8COOC_2H_5$, $-(CH_2)_8CONH_2$, and a radical of the formula $-CH(COOC_2H_5)_2$; carboxyaryl radicals, such as the 4-carboxyphenyl and 3-carboxyphenyl radical and radicals of the formula $4-CH_3OCOC_6H_4-$, $4-C_2H_5OCOC_6H_4-$ and $4-H_2NCOC_6H_4-$; and substituted aralkyl radicals, such as the substituted benzyl radical and the substituted α- and β-phenylethyl radical.

Examples of hydrocarbon radicals $R^4$ are alkyl radicals, such as the methyl, ethyl, n-propyl, iso-propyl, n-butyl, iso-butyl, tert-butyl, n-pentyl, iso-pentyl, neo-pentyl and tert-pentyl radical; hexyl radicals, such as the n-hexyl radical; heptyl radicals, such as the n-heptyl radical; octyl radicals, such as the n-octyl radical, and iso-octyl radicals, such as the 2,2,4-trimethylpentyl radical; nonyl radicals, such as the n-nonyl radical; decyl radicals, such as the n-decyl radical, and dodecyl radicals, such as the n-dodecyl radical; and octadecyl radicals, such as the n-octadecyl radical; alkenyl radicals, such as the vinyl, 1-propenyl, 1-butenyl, 2-butenyl, allyl, isobutenyl, 1-pentenyl and 2-methyl-1-butenyl radical; alkynyl radicals, such as the ethynyl, propargyl, 1-propynyl and 1-butynyl radical; and aryl radicals, such as the phenyl radical.

Examples of substituted hydrocarbon radicals $R^4$, are alkylalkoxy radicals, such as the methylmethoxy, ethylmethoxy, methylethoxy, ethylethoxy, methylisopropoxy, ethylisopropoxy, methylbutoxy and ethylbutoxy radical; aryloxy radicals, such as the phenoxy radical; substituted aryl radicals, such as the 4-bromophenyl, 4-cyanophenyl, 4-nitrophenyl and 4-methoxyphenyl radical; hydroxyalkyl radicals, such as radicals of the formula $HOCH_2CH_2OCH_2CH_2—$, $HOCH_2CH_2—$ and $CH_3CH_2CH(OH)CH_2—$; aminoalkyl radicals, such as the aminomethyl and aminoethyl radical; carboxyalkyl radicals, such as radicals of the formula $—(CH_2)_7COOH$, $—(CH_2)_8COOH$ and $—CH_2COCH_2CH_2COOH$ and esters and amines thereof $—(CH_2)_7COOCH_3$, $—(CH_2)_7COOC_2H_5$, $—(CH_2)_7CONH_2$, $—(CH_2)_8COOCH_3$, $—(CH_2)_8COOC_2H_5$, $—(CH_2)_8CONH_2$, and a radical of the formula $—CH(COOC_2H_5)_2$; carboxyaryl radicals, such as the 4-carboxyphenyl and 3-carboxyphenyl radical and radicals of the formula $4-CH_3OCOC_6H_4—$, $4-C_2H_5OCOC_6H_4—$ and $4-H_2NCOC_6H_4—$.

Examples of hydrocarbon radicals $R^5$ are linear or branched alkylene radicals, such as the methylene, ethylene, propylene, 2-methylpropylene and butylene radical.

Examples of alkyl radicals $R^6$ are the methyl, ethyl, n-propyl, iso-propyl, n-butyl, iso-butyl, tert- butyl, n-pentyl, iso-pentyl, neo-pentyl and tert-pentyl radical; hexyl radicals, such as the n-hexyl radical; heptyl radicals, such as the n-heptyl radical; and octyl radical, such as the n-octyl radical.

The radicals $R^4$ are substituents of the aromatic and heteroaromatic radical A or A' and, for example, if A or A' is an aromatic six-membered ring, such as the phenyl radical, can be in the ortho-, meta- or para- position.

Examples of catalysts are those of the formula
$PtX_aY_b$, where a=2 or 4 and b=2, 1 or 0,
$PdX_aY_b$, where a=1 or 2 and b=0 or 1,
$RuX_aY_b$, where a=1, 2, 3 or 4 and b=0, 1, 2 or 3,
$RhX_aY_b$, where a=1, 2 or 3 and b=0, 1 or 2,
$OsX_aY_b$, where a=3 or 4 and b=0, 1, 2 or 3,
$IrX_aY_b$, where a=1, 2, 3 or 4 and b=0, 1, 2 or 3,
in which X and Y have the meaning given above for these symbols.

Preferred catalysts are the triazenido complexes, in particular with the ligand ANNNR, and the pentazadienido complexes with the ligand $ANNNNNA^1$. Preferred examples of the triazene ligands ANNNR are those of the formula $C_6H_5NNN(CH_2)_xCH_3$, $p-NO_2-C_6H_4NNN(CH_2)_xCH_3$, $p-CN-C_6H_4NNN(CH_2)_xCH_3$ and $p-CH_3(CH_2)_x-C_6H_4NNN(CH_2)_xCH_3$ in which x is 1, 3, 5, 7, 11 or 17, in particular, 1, 5, 7 or 11.

Preferred examples of the ligands $ANNNNNA^1$ are those of the formula $p-Br-C_6H_4NNNNNC_6H_4-Br-p$ and $p-CH_3O-C_6H_4NNNNNC_6H_4-OCH_3-p$.

Preferred examples of catalysts are those of the formula
$Pt[C_6H_5NNN(CH_2)_xCH_3]_4$
$Pt[p-NO_2-C_6H_4NNN(CH_2)_xCH_3]_4$
$Pt[p-CN-C_6H_4NNN(CH_2)_xCH_3]_4$
1,5-cyclooctadiene·$Pt[C_6H_5NNN(CH_2)_xCH_3]_2$
1,5-cyclooctadiene·$Pt[p-NO_2-C_6H_4NNN(CH_2)_xCH_3]_2$
1,5-cyclooctadiene·$Pt[p-CN-C_6H_4NNN(CH_2)_xCH_3]_2$
$Pd[C_6H_5NNN(CH_2)_xCH_3]_2$
$Pd[p-NO_2-C_6H_4NNN(CH_2)_xCH_3]_2$
$Pd[p-CN-C_6H_4NNN(CH_2)_xCH_3]_2$
$(C_6H_5P)_3Ru[C_6H_5NNN(CH_2)_xCH_3]_2$
$(C_6H_5P)_3Ru[p-NO_2-C_6H_4NNN(CH_2)_xCH_3]_2$
$(C_6H_5P)_3Ru[p-CN-C_6H_4NNN(CH_2)_xCH_3]_2$
$(C_6H_5P)_3Rh[C_6H_5NNN(CH_2)_xCH_3]$
$(C_6H_5P)_3Rh[p-NO_2-C_6H_4NNN(CH_2)_xCH_3]$
$(C_6H_5P)_3Rh[p-CN-C_6H_4NNN(CH_2)_xCH_3]$
$Pt[p-Br-C_6H_4NNNNNC_6H_4-Br-p]_4$
$Pt[p-CH_3O-C_6H_4NNNNNC_6H_4-OCH_3-p]_4$
1,5-cyclooctadiene·$Pt[p-Br-C_6H_4NNNNNC_6H_4-Br-p]_2$
1,5-cyclooctadiene·$Pt[p-CH_3O-C_6H_4NNNNNC_6H_4-OCH_3-p]_2$
$Pt[p-CH_3(CH_2)_x-C_6H_4NNN(CH_2)_xCH_3]_2$,
in which x is 1, 3, 5, 7, 11 or 17, in particular 1, 5, 7 or 11, the above mentioned triazenido complexes of platinum being particularly preferred.

The preparation of the triazenido complexes of transition metals, with the exception of the aryl-alkyl-triazenido complexes of transition metals, and of the tetrazenido complexes of transition metals, of the tetrazadienido complexes of transition metals and of the pentazadienido complexes of transition metals and of the pentazadienido complexes of transition metals is known and is described in D. S. Moore et al., Advances in Inorganic Chemistry and Radiochemistry, Volume 30, pages 1–68, 1986.

The preparation of the triazenes, tetrazenes, tetrazadienes and pentazadienes is known and is described in T. P. Ahern et al., Can. J. Chem. 55, 1701 (1977) and M. A. Kelly et al., J. Chem. Soc., Perkin Trans. II, 1649 (1982).

Examples of triazenes of the formula ANNNHR' which are employed in the preparation of the aryl-alkyl-triazenido complexes of the formula $M'X'_aY_b$ are
$C_6H_5NNNH(CH_2)_xCH_3$
$p-NO_2-C_6H_4NNNH(CH_2)_xCH_3$
$p-CN-C_6H_4NNNH(CH_2)_xCH_3$
$p-CH_3-C_6H_4NNNH(CH_2)_xCH_3$
$p-CH_3(CH_2)_x-C_6H_4NNNH(CH_2)_xCH_3$
$p-H_3COCO-C_6H_4NNNH(CH_2)_xCH_3$
$p-CH_3NHCO-C_6H_4NNNH(CH_2)_xCH_3$
$p-CH_3O-C_6H_4NNNH(CH_2)_xCH_3$ and
$p-(CH_3)_2N-C_6H_4NNN(CH_2)_xCH_3$, in which
$C_6H_5NNNH(CH_2)_xCH_3$,
$p-NO_2-C_6H_5NNNH(CH_2)_xCH_3$
$p-CN-C_6H_5NNNH(CH_2)_xCH_3$ and
$p-CH_3(CH_2)_x-C_6H_4NNNH(CH_2)_xCH_3$
(x is 1, 3, 5, 7, 11 or 17, in particular 1, 5, 7 or 11) being preferred examples.

Examples of transition metal compounds of the formula $M'Y_d$ which are employed in the preparation of the aryl-alkyl-tria-zenido complexes of the formula $M'X'_aY_b$ are $PtCl_2$, $PtI_2$, $[(C_6H_5)_3P]_2PtCl_2$, $[(C_2H_5)_3P]_2PtCl_2$, $PtCl_4$, $Pt(H_2NCH_2CH_2NH_2)Cl_2$, $Pt(NH_3)_2Cl_2$, $PtBr_2$, $PtI_2$, 1,5-cyclooctadiene·$PtCl_2$, $Pd(CH_3CN)_2Cl_2$, $PdBr_2$, 1,5-cyclooctadiene·$PdCl_2$, $[(C_6H_5)_3P]_2PdCl_2$, $PdCl_2$, $RuCl_3$, $Ru(NH_3)_6Cl_2$, $[(C_6H_5)_3P]_3RuCl_2$, $RhCl_3$, $RhBr_3$, $[(C_6H_5)_3P]_3RhCl$, (1,5-cyclooctadiene)$_2$Pt,1,3-divinyl-1,1,3,3-tetramethyldisiloxaneplatinum complex (for example $Pt_2[1,3$-divinyl-1,1,3,3-tetramethyldisiloxane$]_3$), Pd[bis-(1,2-diphenylphosphinoethane)], hexarhodium hexadecacarbonyl and triruthenium dodecacarbonyl, in which $PtCl_4$, 1,5-cyclooctadiene·$PtCl_2$, $PtI_2$, 1,3-divinyl-1,1,3,3-tetramethyldisiloxaneplatinum complex, $PdCl_2$, $[(C_6H_5)_3P]_3RuCl_2$ and $[(C_6H_5)_3P]_3RhCl$ is preferred.

Examples of bases which are employed in the preparation of the aryl-alkyl-triazenido complexes of the formula $M'X'_aY_b$ are n-butyllithium, triethylamine, piperidine, pyridine, $NaOCH_3$ and $NaNH_2$, in which n-butyllithium and triethylamine being preferred.

The process for the preparation of the aryl-alkyl-triazenido complexes $M'X'_aY_b$ is preferably carried out in the presence of organic solvents, such as n-hexane, toluene, methylene chloride, chloroform, acetone or tetrahydrofuran, but can also be carried out in the presence of a mixture of water and organic solvent, such as methanol, ethanol, isopropanol or tetrahydrofuran.

The process for the preparation of the aryl-alkyl-triazenido complexes $M'X'_a Y_b$ is preferably carried out at temperatures of 0° C. to 50° C. under the pressure of the surrounding atmosphere and with exclusion of light. The organic solvent or the mixture of organic solvent and water is preferably removed after the reaction. The invention furthermore relates to a process for activation of the catalysts according to the invention by heating at temperatures of 50° C. to 250° C. and/or by irradiation with light and/or by addition of Brönsted acids and/or by addition of acid-forming agents.

The activation temperature of the catalysts according to the invention depends on the ligand X and the transition metal atom M of the particular complex. Ultraviolet light is preferred as the light with which the catalysts according to the invention can be activated. There are a large number of commercially available lamps which emit ultraviolet light in the range from 200 to 400 nm. The catalysts according to the invention can be activated by heating at temperatures of 50° C. to 250° C. and additionally by irradiation with light, preferably ultraviolet light. Examples of Brönsted acids are acetic acid, $HNO_3$, $H_2SO_4$ and HCl. Iodonium or sulfonium salts are preferably used as acid-forming agents. Those iodonium or sulfonium salts such as are described in German Applications P 41 42 327.5 and P 42 19 376.1 are preferably used. Examples of iodonium and sulfonium salts are those of the formula

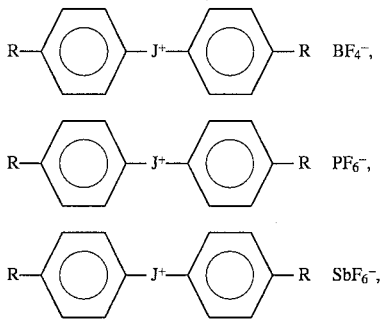

in which R represents a $C_1$ to $C_{18}$-hydrocarbon radial, such as the n-dodecyl radical,

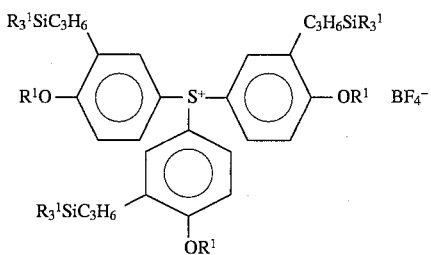

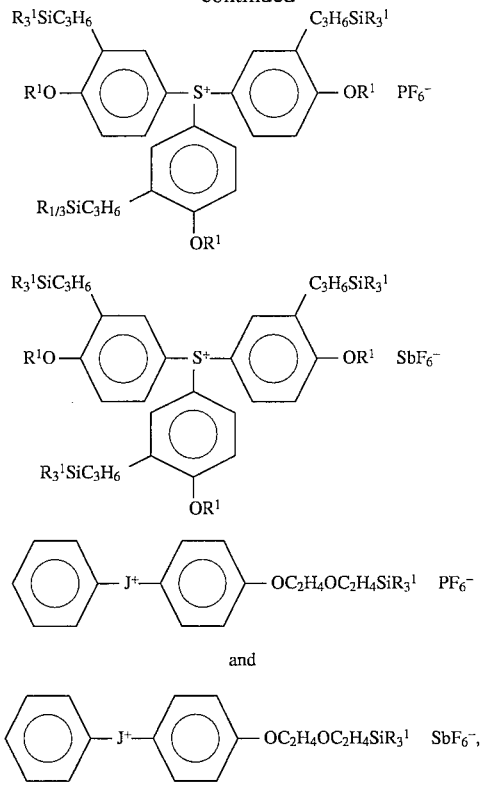

and

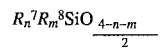

in which $R^1$ represents a $C_1$ to C4-hydrocarbon radical, such as the n-butyl, methyl, ethyl or propyl radical.

The iodonium and sulfonium salts eliminate strong acids under irradiation with light, preferably ultraviolet light.

The catalysts according to the invention can be used in all crosslinkable organopolysiloxane compositions in which it has also been possible to use catalysts which promote the addition of Si-bonded hydrogen onto an aliphatic multiple bond.

The invention therefore relates to crosslinkable organopoly-siloxane compositions comprising
(1) organopolysiloxanes which contain radicals with aliphatic carbon-carbon multiple bonds,
(2) organopolysiloxanes with Si-bonded hydrogen atoms or, instead of (1) and (2),
(3) organopolysiloxanes which contain radicals with aliphatic carbon-carbon multiple bonds and Si-bonded hydrogen atoms, and
(4) catalysts according to formula (I).

Radicals with aliphatic carbon-carbon multiple bonds are also understood as meaning radicals with cycloaliphatic carbon-carbon multiple bonds.

Organopolysiloxane (1) which contain radicals with aliphatic carbon-carbon multiple bonds and which are used are preferably linear or branched organopolysiloxanes comprising units of the formula $$R_n^7 R_m^8 SiO_{\frac{4-n-m}{2}}$$

in which
$R^7$ represents a monovalent hydrocarbon radical which has 1 to 18 carbon atoms per radical and is free from aliphatic carbon-carbon multiple bonds and
$R^8$ represents a monovalent hydrocarbon radical which has 2 to 8 carbon atoms per radical and an aliphatic carbon-carbon multiple bond, n is 0, 1, 2 or 3, m is 0, 1, or 2 and the sum of n+m is 0, 1, 2 or 3, with the proviso that an average of at least 2 radical $R^8$ are present per molecule. The organopolysiloxanes (1) preferably have an average viscosity of 100 to 10,000 mPa·s at 25° C.

Examples of hydrocarbon radicals $R^7$ are alkyl radicals, such as the methyl, ethyl, n-propyl, iso-propyl, n-butyl, iso-butyl, tert-butyl, n-pentyl, iso-pentyl, neo-pentyl and tert-pentyl radical; hexyl radicals, such as the n-hexyl radical; heptyl radicals, such as the n-heptyl radical; octyl radicals, such as the n-octyl radical, and iso-octyl radicals, such as the 2,2,4-trimethylpentyl radical; nonyl radicals, such as the n-nonyl radical; decyl radicals, such as the n-decyl radical, and dodecyl radicals, such as the n-dodecyl radical; octadecyl radicals, such as the n-octadecyl radical; cycloalkyl radicals, such as the cyclopentyl, cyclohexyl and cycloheptyl radicals and methylcyclohexyl radicals; aryl radicals, such as the phenyl, naphthyl, anthryl and phenanthryl radical; alkaryl radicals, such as o-, m- and p-tolyl radicals, xylyl radical and ethylphenyl radicals; and aralkyl radicals, such as the benzyl radical and the α- and β-phenylethyl radical.

Examples of radicals $R^8$ are alkenyl radicals, such as the vinyl, 5-hexenyl, 1-propenyl, allyl, 1-butenyl and 1-pentenyl radical; and alkynyl radicals, such as the ethynyl, propargyl and 1-propynyl radical.

Organopolysiloxanes (2) which contain Si-bonded hydrogen atoms and which are used are preferably linear, cyclic or branched organopolysiloxanes comprising units of the formula $$R_e^7 H_f SiO_{\frac{4-e-f}{2}}$$

in which $R^7$ has the meaning given above for this symbol, e is 0, 1, 2 or 3, f is 0, 1 or 2 and the sum of e+f is 0, 1, 2 or 3, with the proviso that an average of at least 2 Si-bonded hydrogen atoms are present per molecule. The organopolysiloxanes (2) preferably have an average viscosity of 10 to 1,000 mPa·s at 25° C.

Organopolysiloxanes (3) which contain aliphatic carbon-carbon multiple bonds and Si-bonded hydrogen atoms and which can be used instead of organopolysiloxanes (1) and (2) are preferably those comprising units of the formula $$R_k^7 SiO_{\frac{4-k}{2}}, R_l^7 R^8 SiO_{\frac{3-l}{2}} \text{ and } R_p^7 HSiO_{\frac{3-p}{2}}$$

in which $R^7$ and $R^8$ have the meaning given above for these symbols, k is 0, 1, 2 or 3, l is 0, 1 or 2 and p is 0, 1 or 2, with the proviso that an average of at least 2 radical $R^8$ and an average of at least 2 Si-bonded hydrogen atoms are present per molecule.

Examples of organopolysiloxanes (3) are those comprising $SiO_{4/2}$, $R^7_3SiO_{1/2}$, $R^7_2R^8SiO_{1/2}$ and $R^7_2HSiO_{1/2}$ units, so-called MQ resins, it being possible for these resins to contain T units ($R^7SiO_{3/2}$) and D units ($R^7_2SiO$).

The organopolysiloxanes (3) preferably have an average viscosity of 100 to 100,000 mPa·s at 25° C. or are solids having molecular weights of 5,000 to 50,000 g/mol.

The catalysts according to the invention are preferably employed in amounts of 1 to 1,000 ppm by weight (parts by weight per million parts by weight), preferably 10 to 100 ppm by weight, in each case calculated as elemental transition metal Pt, Pd, Ru, Rh, Os or Ir and based on the total weight of organopolysiloxanes (1) and (2) or on the total weight of organopolysiloxanes (3).

Although not preferred, inhibitors can also be used in the crosslinkable organopolysiloxane compositions. Examples of inhibitors are 1,3-divinyl-1,1,3,3-tetramethyldisiloxane, benzotriazole, dialkylformamides, alkylthioureas, methyl ethyl ketoxime, organic or organosilicon compounds having a boiling point of at least 25° C. under 1021 mbar (absolute) and at least one aliphatic triple bond according to U.S. Pat. No. 3,445,420, such as 1-ethynylcyclohexan-1-ol, 2-methyl-3-butyn-2-ol, 3-methyl-1-pentyn-3-ol, 2,5-dimethyl-3-hexyne-2,5-diol and 3,5-dimethyl-l-hexyn-3-ol, inhibitors according to U.S. Pat. No. 2,476,166, such as a mixture of diallyl maleate and vinyl acetate, and inhibitors according to U.S. Pat. No. 4,504,645, such as maleic acid monoesters.

The catalysts according to the invention furthermore can be employed in all processes for the reaction of organosilicon compounds containing Si-bonded hydrogen atoms with organic compounds containing aliphatic multiple bonds in which it has also hitherto been possible to employ catalysts which promote the addition of Si-bonded hydrogen onto an aliphatic multiple bond. The invention therefore relates to a process for the reaction of organosilicon compounds containing Si-bonded hydrogen atoms with organic compounds containing aliphatic multiple bonds in the presence of catalysts according to formula (I).

Organic compounds with aliphatic multiple bonds are also to be understood as meaning organic compounds with cycloaliphatic multiple bonds.

Examples of organosilicon compounds containing Si-bonded hydrogen atoms are silanes with one Si-bonded hydrogen atom per molecule, such as trichlorosilane, dimethylchlorosilane, dimethylethoxysilane, methyldiethoxysilane, methyldichlorosilane and triethoxysilane, and organopolysiloxanes with at least one Si-bonded hydrogen atom per molecule, such as α,w-dihydrido[dimethylpolysiloxane], tetramethyldisiloxane, tetramethylcyclotetrasiloxane, copolymers of trimethylsiloxane and methylhydridosiloxane units, copolymers of trimethylsiloxane, dimethylsiloxane and methylhydridosiloxane units and trimethylsiloxyhydridosilane.

Examples of organic compounds containing aliphatic multiple bonds are compounds with an aliphatic carbon-carbon double bond, such as styrene, allyl glycidyl ether, allyl cyanide, allyl acetate, allylsuccinic anhydride, glycol monoallyl ether, allyl methacrylate, allylamine and cyclohexene, and compounds with an aliphatic carbon-carbon triple bond, such as acetylene and butynol.

Preparation of the triazenes (in an aqueous system)

0.25 mol of the particular aniline derivative mentioned in Table I was dissolved in 200 ml of 10% strength aqueous hydrochloric acid and the solution was then stirred with 1 g of active charcoal for 5 minutes and filtered. A solution of 17.25 g (0.25 mol) of sodium nitrite in 30 g of water was added to the filtrate at 0° C. with exclusion of light. After 15 minutes, 1 mol of the particular alkylamine mentioned in Table 1 was added dropwise at 0° C. and the mixture was stirred at room temperature for 2 hours. After addition of organic solvent, the mixture was extracted by shaking with 3×50 ml of water (or with dilute acetic acid if required) and the organic phase was dried over sodium sulfate. After filtration, the filtrate was concentrated at room temperature in a rotary evaporator under reduced pressure. Possible contents of pentazadiene by-products can be separated off as a solid in methanolic solution at −65° C. The products mentioned in Table 1 were obtained with yields of between 60% and 80%.

Preparation of the triazenes (in an organic system)

0.2 mol of the particular aniline derivative mentioned in Table 1 was dissolved in 100 ml of acetone and the solution was then stirred. with 1 g of active charcoal for 5 minutes and filtered. 24.59 g (0.25 mol) of anhydrous sulfuric acid were added to the filtrate at −5° C. with exclusion of light and moisture, and the mixture was stirred for 20 minutes. 20.62 g (0.2 mol) of n-butyl nitrite were then added dropwise and the mixture was stirred at 0° C. for an additional 2 hours. Finally, 0.5 mol of the particular alkylamine mentioned in Table 1 was added dropwise and the mixture was stirred for an additional 2 hours. The organic phase was extracted by shaking three times with 50 ml of aqueous hydrochloric acid and the extract was dried over sodium sulfate and concentrated to constant weight on a rotary evaporator under reduced pressure. The products mentioned in Table 1 were obtained in yields of between 70% and 80%.

TABLE 1

| Aniline derivative | Alkylamine | Triazene |
| --- | --- | --- |
| Aniline | n-Hexylamine | 1-Phenyl-3-n-hexyl-1-triazene |
| p-Nitroaniline | n-Octylamine | 1-[4-Nitrophenyl]-3-n-octyl-1-triazene |
| p-Cyanoaniline | n-Hexylamine | 1-[4-Cyanophenyl]-3-n-hexyl-1-triazene |

Preparation of the pentazadienes 20 mmol of the particular aniline derivative mentioned in Table 2 were dissolved in 40 ml of 10% strength aqueous hydrochloric acid (109 mmol) and the solution was stirred with 0.5 g of active charcoal for 5 minutes and filtered. A solution of 1.38 g (20 mmol) of sodium nitrite in 10 ml of water was added to the filtrate at −5° C. with exclusion of light, and, after 15 minutes, 10 ml of a 25% strength ammonia solution (147 mmol) were metered in at 0° C. The mixture was stirred at room temperature for one hour. After addition of 100 ml of organic solvent, the mixture was extracted by shaking three times with 50 ml of water (or with dilute acetic acid if required) and the organic phase was dried over sodium sulfate. The pentazadienes were reacted with the transition metals without purification (risk of explosion).

TABLE 2

| Aniline derivative | Product |
| --- | --- |
| Aniline | 1,5-Diphenyl-1,4-pentazadiene |
| p-Bromo-aniline | 1,5-di[4-Bromophenyl]-1,4-pentazadiene |
| p-Methoxy-aniline | 1,5-di[4-Methoxyphenyl]-1,4-pentazadiene |

EXAMPLE 1

2.5 g (12.1 mmol) of 1-phenyl-3-n-hexyl-1-triazene, the preparation of which has been described above, were initially introduced into the reaction vessel with 20 ml of n-hexane at −10° C. with exclusion of light. 8 ml of a 1.6 molar solution of n-butyllithium (12.8 mmol) in hexane were slowly metered in under a nitrogen atmosphere. After 20 minutes, a solution of 1.02 g (3.02 mmol) of PtCl$_4$ in 50 ml of tetrahydrofuran was added dropwise and the mixture was stirred at room temperature for 24 hours. The solution was evaporated on a rotary evaporator at room temperature and under reduced pressure, the residue was taken up in 50 ml of n-hexane, the mixture was filtered and the filtrate was evaporated again on a rotary evaporator at room temperature. 2.44 g (80% yield) of the tetrakis(1-phenyl3-n-hexyl-1-triazenido)-platinum complex were obtained.

EXAMPLE 2

The procedure of Example 1 was repeated, with the modification that 6.05 mmol instead of 12.1 mmol of 1-phenyl-3-n-hexyl-1-triazene, 6.4 mmol instead of 12.8 mmol of n-butyllithium and 3.02 mmol of 1,5-cyclooctadiene·PtCl$_2$ instead of 3.02 mmol of PtCl$_4$ were employed. The 1,5-cyclooctadiene-bis(1-phenyl-3-n-hexyl-1-triazenido)platinum complex was obtained.

EXAMPLE 3

55.69 g (0.2 mol) of 1-[4-nitrophenyl]-3-n-octyl-1-triazene, the preparation of which has been described above, was initially introduced into 300 ml of toluene with exclusion of light and moisture, and 20.24 g (0.2 mol) of dry triethylamine were added. After 10 minutes, a solution of 16.84 g (0.05 mol) of PtCl$_4$ in 40 ml of tetrahydrofuran was added dropwise and the mixture was stirred at room temperature for 24 hours (or at 40° C. for 8 hours). The solution was concentrated to half at room temperature and under reduced pressure, the concentrate was cooled to −10° C. and filtered, and the filtrate was finally evaporated to constant weight on a rotary evaporator. 54.07 g (83% yield) of the tetrakis[1-(4-nitrophenyl)-3-n-octyl-1-triazenido]platinum complex were obtained.

EXAMPLE 4

The procedure of Example 3 was repeated, with the modification that 0.2 mol of 1-[4-cyanophenyl]-3-n-hexyl-1-triazene, the preparation of which has been described above, was employed instead of 0.2 mol of 1-[4-nitrophenyl]-3-n-octyl-1-triazene. The tetrakis[1-(4-cyanophenyl)-3-n-hexyl-1-triazenido]platinum complex was obtained.

EXAMPLE 5

The procedure of Example 3 was repeated, with the modification that 0.1 mol instead of 0.2 mol of 1-(4-nitrophenyl)-3-n-octyl-1-triazene, 0.1 mol instead of 0.2 mol of triethylamine and 0.05 mol of 1,5-cyclooctadiene·PtCl$_2$ instead of 0.05 mol of PtCl$_4$ were employed. The 1,5-cyclooctadiene-bis[1-(4-nitro-phenyl)-3-n-octyl-1-triazenido]platinum complex was obtained.

EXAMPLE 6

4.62 g (22.5 mmol) of 1-phenyl-3-n-hexyl-1-triazene, the preparation of which has been described above, were initially introduced into 20 ml of toluene at −10° C. with exclusion of light. 15.6 ml of a 1.6 molar solution of n-butyllithium (25 mmol) in hexane were slowly metered in under a nitrogen atmosphere. After 20 minutes, a solution of 2 g of PdCl$_2$ in 150 ml of tetrahydrofuran was added dropwise and the mixture was stirred at room temperature for 48 hours. The solution was evaporated on a rotary evaporator at room temperature under reduced pressure, the residue was suspended with 100 ml of n-hexane at −45° C. and filtered off and the filtrate was evaporated again on a rotary evaporator at room temperature. 4.17 g (72% yield) of the bis(1-phenyl-3-n-hexyl-1-triazenido)palladium complex were obtained.

EXAMPLE 7

1.06 g (5.16 mmol) of 1-phenyl-3-n-hexyl-1-triazene, the preparation of which has been described above, were initially introduced into 20 ml of toluene at −10° C. with exclusion of light. 3.75 ml of a 1.6 molar solution of n-butyllithium (6 mmol) in hexane were slowly metered in under a nitrogen atmosphere. After 20 minutes, a solution of 2.47 g (2.58 mmol) of tris(triphenylphosphine)ruthenium(II) chloride in 150 ml of tetrahydrofuran was added dropwise, and the mixture was stirred at room temperature for 48 hours. The solution was evaporated on a rotary evaporator at room temperature under reduced pressure, the residue was suspended with 100 ml of n-hexane at −45° C. and filtered off and the filtrate was evaporated again on a rotary evaporator at room temperature. 2.27 g (68% yield) of the tris-(triphenylphosphine)bis(1-phenyl-3-n-hexyl-1-triazenido)ruthenium complex were obtained.

EXAMPLE 8

The procedure of Example 7 is repeated, with the modification that 2.39 g of tris(triphenylphosphine)-rhodium(I) chloride instead of 2.47 g of tris(triphenylphosphine)ruthenium(II) chloride, 0.53 g (2.58 mmol) instead of 1.06 g (5.16 mmol) of 1-phenyl-3-n-hexyl-1-triazene and 1.88 ml (3 mmol) instead of 3.75 ml (6 mmol) of n-butyllithium were employed. The tris-(triphenylphosphine)-1-phenyl-3-n-hexyl-1-triazenido-rhodium complex was obtained.

EXAMPLE 9

6 ml of a 1.6 molar solution of n-butyllithium (9.6 mmol) in hexane were slowly metered into 3 g (7.4 mmol) of 1,5-di(4-bromophenyl)-1,4-pentazadiene, the preparation of which has been described above, dissolved in 200 ml of toluene, with exclusion of light and at 0° C. under a nitrogen atmosphere. After 20 minutes, a solution of 0.623 g (1.85 mmol) of $PtCl_4$ in 50 ml of tetrahydrofuran was added dropwise and the mixture was stirred at room temperature for 24 hours. The solution was evaporated on a rotary evaporator at room temperature under reduced pressure, the residue was dissolved in 100 ml of toluene, the solution was cooled to −45° C. and filtered and the filtrate was evaporated again on a rotary evaporator at room temperature. 2.68 g (80% yield) of the tetrakis[1,5-di(4-bromophenyl)-1,4-pentazadienido]platinum complex were obtained.

EXAMPLE 10

The procedure of Example 9 was repeated, with the modification that 3.7 mmol of 1,5-cyclooctadiene·$PtCl_2$ were employed instead of 1.85 mmol of $PtCl_4$. The 1,5-cyclooctadiene-bis[1,5-di(4-bromophenyl)-1,4-pentazadienido]platinum complex was obtained.

EXAMPLE 11

6.41 g (22.5 mmol) of 1,5-di(4-methoxyphenyl)-1,4-pentazadiene, the preparation of which has been described above, were initially introduced into 20 ml of toluene at −10° C. with exclusion of light. 15.6 ml of a 1.6 molar solution of n-butyllithium (25 mmol) in hexane were slowly metered in under a nitrogen atmosphere. After 20 minutes, a solution of 2 g (11.25 mmol) of $PdCl_2$ in 150 ml of tetrahydrofuran was added dropwise and the mixture was stirred at room temperature for 48 hours. The solution was evaporated on a rotary evaporator at room temperature under reduced pressure, the residue was suspended with 100 ml of n-hexane at −45° C. and filtered off and the filtrate was evaporated again on a rotary evaporator at room temperature. 5.46 g (72% yield) of the bis[1,5-di(4-methoxyphenyl)-1,4-pentazadienido]-palladium complex were obtained.

EXAMPLE 12

2 mg ($1.9\times10^{-6}$ mol) of tetrakis(1-phenyl-3-n-hexyl-1-triazenido)platinum complex, the preparation of which has been described in Example 1, were dissolved in 0.1 ml of toluene and the solution was then added to 7.46 g of α,w-divinyldimethylpolysiloxane having a viscosity of 500 mPa·s at 25° C. The solvent was removed at room temperature under reduced pressure. 0.187 g of a copolymer of trimethylsiloxane and methylhydridosiloxane units having a viscosity of 33 mPa·s at 25° C. and containing 1.12% by weight of Si-bonded hydrogen was added to the reaction mixture which remained, so that the mixture contained 50 ppm by weight of platinum, calculated as the element. The entire mixture was stable at room temperature and with exclusion of light for at least 6 weeks. After irradiation with ultraviolet light (UVA=56 mW/cm$^2$, UVB=12 mW/cm$^2$) for 5 minutes, complete crosslinking of the composition was achieved (the extractable contents, that is the non-crosslinked contents, are less than 5% by weight). A transparent product insoluble in organic solvents was obtained.

EXAMPLE 13

The procedure of Example 12 was repeated, with the modification that after heating at 80° C. for 8 minutes, complete crosslinking of the composition was achieved (the extractable contents, that is the non-crosslinked contents, are less than 5% by weight). A transparent product insoluble in organic solvents was obtained.

EXAMPLE 14

The procedure of Example 12 was repeated, with the modification that after heating at 100° C. for 4.5 minutes, complete crosslinking of the composition was achieved (the extractable contents, or the non-crosslinked contents, are less than 5% by weight). A transparent product insoluble in organic solvents was obtained.

EXAMPLE 15

The procedure of Example 12 was repeated, with the modification that after heating at 120° C. for 2.3 minutes, complete crosslinking of the composition was achieved (the extractable contents, or the non-crosslinked contents, are less than 5% by weight). A transparent product insoluble in organic solvents was obtained.

EXAMPLE 16

The procedure of Example 12 was repeated, with the modification that an α,w-divinyldimethylpolysiloxane having a viscosity of 1,000 mPa·s at 25° C. instead of 500 mPa·s at 25° C. was employed. After irradiation with ultraviolet light (UVA=56 mW/cm$^2$, UVB=12 mW/cm$^2$) for 5 minutes, complete crosslinking of the composition was achieved (the extractable contents, or non-crosslinked contents, are less than 5% by weight). A transparent product insoluble in organic solvents was obtained.

EXAMPLE 17

The procedure of Example 12 was repeated, with the modification that 4.9 mg ($3.7 \times 10^{-6}$ mol) of tris(triphenylphosphine)bis-1-phenyl-3-n-hexyl-1-triazenido)ruthenium complex, the preparation of which has been described in Example 7, were employed instead of 2 mg of tetrakis(1-phenyl-3-n-hexyl-1-triazenido)platinum complex. The mixture contained 50 ppm by weight of ruthenium, calculated as the element. The entire mixture was stable at room temperature and with exclusion of light for at least 9 weeks. After heating at 180° C. for 31 minutes, complete crosslinking of the composition was achieved (the extractable contents, or non-crosslinked contents, are less than 5% by weight). A clear brittle composition was obtained.

EXAMPLE 18

The procedure of Example 17 was repeated, with the modification that an α,w-divinyldimethylpolysiloxane having a viscosity of 1,000 mPa·s at 25° C. instead of 500 mPa·s at 25° C. was employed. The entire mixture was stable at room temperature and with exclusion of light for at least 9 weeks. After heating at 180° C. for 31 minutes, complete crosslinking of the composition was achieved (the extractable contents, or non-crosslinked contents, are less than 5% by weight). A clear brittle composition was obtained.

EXAMPLE 19

The procedure of Example 12 was repeated, with the modification that 1.85 mg ($3.6 \times 10^{-6}$ mol) of bis-(1-phenyl-3-n-hexyl-1-triazenido)palladium complex, the preparation of which has been described in Example 6, were employed instead of 2 mg of tetrakis(1-phenyl-3-n-hexyl-1-triazenido)platinum complex. The mixture contained 50 ppm by weight of palladium, calculated as the element. The entire mixture was stable at room temperature and with exclusion of light for at least 9 weeks. After heating at 170° C. for 13 minutes, complete crosslinking of the composition was achieved (the extractable contents, or non-crosslinked contents, are less than 5% by weight). A clear brittle composition was obtained.

EXAMPLE 20

The procedure of Example 19 was repeated, with the modification that an α,w-divinyldimethylpolysiloxane having a viscosity of 1,000 mPa·s at 25° C. instead of 500 mPa·s at 25° C. was employed. The entire mixture was stable at room temperature and with exclusion of light for at least 9 weeks. After heating at 170° C. for 13 minutes, complete crosslinking of the composition was achieved (the extractable contents, or non-crosslinked contents, are less than 5% by weight). A clear brittle composition was obtained.

EXAMPLE 21

A solution of 0.636 mg ($1.0 \times 10^{-6}$ mol) of tetrakis(1-phenyl-3-n-hexyl-1-triazenido)platinum complex, the preparation of which has been described in Example 1, in 0.1 ml of toluene was dissolved in 0.5 g of an organopolysiloxane resin comprising $SiO_2$, trimethylsiloxane, dimethylvinylsiloxane and methylphenylsiloxane units, having a viscosity of 1,600 mPa·s at 25° C. and containing 7.6% by weight of Si-bonded vinyl groups. The solvent was removed at room temperature under reduced pressure, and 5 g of an organopolysiloxane resin comprising $SiO_2$, trimethylsiloxane, dimethylhydridosiloxane and methylphenylsiloxane units, having a viscosity of 2,000 mPa·s at 25° C. and containing 0.2% by weight of Si-bonded hydrogen were added to the reaction mixture which remained such that the mixture contained 21 ppm by weight of platinum, calculated as the element. The entire mixture was stable at room temperature and with exclusion of light for at least 6 weeks. After heating at 170° C. for 15 minutes, with thorough mixing, complete crosslinking of the composition was achieved. A clear insoluble substance was obtained.

EXAMPLE 22

The procedure of Example 21 was repeated, with the modification that 1.41 mg ($1.0 \times 10^{-6}$ mol) of tris(triphenylphosphine)bis(1-phenyl-3-n-hexyl-1-triazenido)ruthenium complex, the preparation of which has been described in Example 7, were employed instead of 0.636 mg of tetrakis(1-phenyl-3-n-hexyl-1triazenido)platinum complex. The mixture contained 20 ppm by weight of ruthenium, calculated as the element. The mixture was stable at room temperature and with exclusion of light for at least 9 weeks. After heating at 180° C. for 30 minutes, with thorough mixing, complete crosslinking of the composition was achieved. A clear insoluble substance was obtained.

EXAMPLE 23

The procedure of Example 21 was repeated, with the modification that 0.53 mg ($1.0 \times 10^{-6}$ mol) of bis(1-phenyl-3-n-hexyl-1-triazenido)palladium complex, the preparation of which has been described in Example 6, was employed instead of 0.636 mg of tetrakis(1-phenyl-3-n-hexyl-1-triazenido)platinum complex. The mixture contained 20 ppm by weight of palladium, calculated as the element. The mixture was stable at room temperature and with exclusion of light for at least 9 weeks. After heating at 170° C. for 30 minutes, with thorough mixing, complete crosslinking of the composition was achieved. A clear insoluble substance was obtained.

EXAMPLE 24

4 g of an organopolysiloxane resin of the formula $(SiO_2)_{610}\text{-}(Me_3SiO_{1/2})_{232}(EtO_{1/2})_{414}(HMe_2SiO_{1/2})_{156}(ViMe_2SiO_{1/2})_{100}$ were dissolved in 16 g of toluene at room temperature, the solution was filtered, and 5.19 mg of tetrakis(1-phenyl-3-n-hexyl-1-triazenido) platinum complex were admixed, while stirring, such that the mixture contained 50 ppm by weight of platinum, calculated as the element. After heating at 60° C. for 10 hours, complete crosslinking of the composition was achieved. A stiff, slightly yellow-colored gel was obtained.

EXAMPLE 25

3.55 mg ($1.96 \cdot 10^{-6}$ mol) of tetrakis[1,5-di(4-bromophenyl)-1,4-pentazadienido]platinum complex, the preparation of which has been described in Example 9, were dissolved in 0.1 ml of toluene and the solution was then added to 7.46 g of α, w-divinyldimethylpolysiloxane having a viscosity of 500 mPa·s at 25° C. The solvent was removed at room temperature under reduced pressure. 0.187 g of a copolymer of trimethylsiloxane and methylhydridosiloxane units having a viscosity of 33 mPa·s at 25° C. and containing 1.12% by weight of Si-bonded hydrogen was added to the reaction mixture which remained, such that the mixture contained 50 ppm by weight of platinum calculated as the element. The entire mixture was stable at room temperature and with exclusion of light for at least 6 weeks. After heating at 100°

C. for 3.5 minutes, complete crosslinking of the composition was achieved (the extractable contents, that is the non-crosslinked contents, are less than 5% by weight). A transparent product insoluble in organic solvents was obtained.

EXAMPLE 26

The procedure of Example 25 was repeated, with the modification that the mixture was crosslinked in the course of 3 minutes by irradiation with ultraviolet light (UVA=56 mW/cm$^2$, UVB=12 mW/cm$^2$) instead of by heating at 100° C.

EXAMPLE 27

The procedure of Example 25 was repeated, with the modification that 6.56 mg of bis[1,5-di(4-methoxyphenyl)-1,4-pentazadienido]-palladium complex, the preparation of which has been described in Example 11, were employed instead of 3.55 mg of tetrakis[1,5-di(4-bromophenyl)-1,4-pentazadienido]platinum complex. The mixture contained 100 ppm by weight of palladium, calculated as the element. The mixture was stable at room temperature and with exclusion of light for at least 6 weeks. After heating at 150° C. for 22 minutes, complete crosslinking of the composition was achieved (the extractable contents, that is the non-crosslinked contents, are less than 5% by weight). A transparent product insoluble in organic solvents was obtained.

EXAMPLE 28

140 g (0.85 mol) of hydridotriethoxysilane were mixed with 100 g (0.88 mol) of allyl glycidyl ether, and 10 g of this mixture were initially introduced into a reaction vessel at 95° C. under normal pressure with 100 mg (9.5×10$^{-5}$ mol) of tetrakis(1-phenyl-3-n-hexyl-1-triazenido) platinum complex. The remainder of the above mentioned was added dropwise to the mixture in the course of 80 minutes, the temperature rose to 160° C. When the addition was complete, the reaction mixture was stirred at 150° C. for an additional 30 minutes. After distillation, 3-glycidoxypropyltriethoxysilane was obtained as a colorless, liquid product in a 62.6% yield.

EXAMPLE 29

0.8 mg (7.0·10$^{-7}$ mol) of tetrakis(1-phenyl-3-n-hexyl-1-triazenido) platinum complex was dissolved in 0.1 ml of toluene, the solution was added to 7.46 g of α,w-divinyldimethylpolysiloxane having a viscosity of 500 mPa·s at 25° C., and 0.3 g of a 50% strength solution of a sulfonium salt of the formula

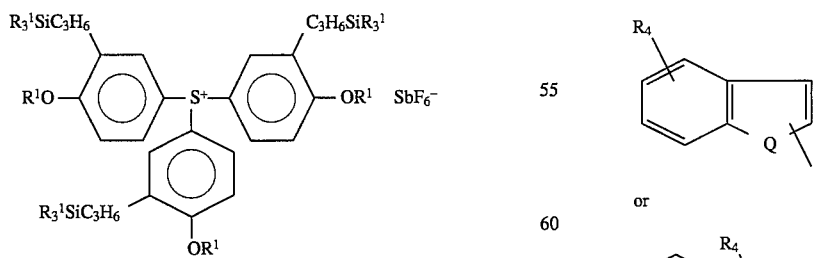

(R$^1$=n-butyl radical) in hexane (20 ppm by weight, based on the mixture) was added. The solvents were removed at room temperature under reduced pressure, and 0.187 g of a copolymer comprising trimethylsiloxane and methylhydridosiloxane units, having a viscosity of 33 mPa·s at 25° C.

and containing 1.12% by weight of Si-bonded hydrogen was added to the reaction mixture which remained (20 ppm by weight, based on the total weight of the mixture). The mixture is stable at room temperature and with exclusion of light for at least 6 weeks. Complete crosslinking (extractable contents<5% by weight) was achieved by UV light (UVA= 56 mW/cm$^2$, UVB=12 mW/cm$^2$) in 3.2 minutes. A transparent, insoluble product was obtained.

What is claimed is:

1. A transition metal complex of the general formula $$M'X'_a Y_b \qquad (II),$$

in which

M' is Pt, Pd, Rh and Ru,

X' represents a 1-triazene ligand of the general formula

ANNNR' in which

R' represents a monovalent, optionally substituted hydrocarbon radical having 1 to 18 carbon atoms per radical, excluding aromatic hydrocarbon radicals in which the aromatic part is bonded directly to the nitrogen atom, or a radical of the formula —SiR$^6_c$(OR$^6$)$_{3-c}$, and A represents a radical of the formula

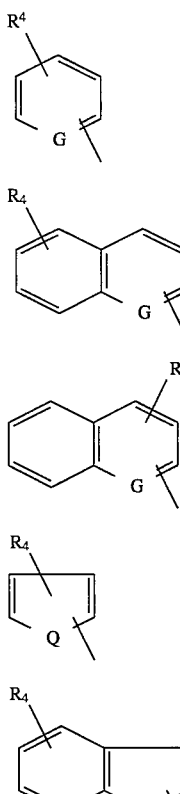

in which

G is CH or N and

Q is S, O or NH, $R^4$ represents a monovalent optionally substituted hydrocarbon radical having 1 to 12 carbon atoms per radical or a radical of the formula —F, —Cl, —Br, —I, —H, —$NH_2$, —$NR^6{}_2$, —$NO_2$, —OH, —$OR^6$, —SH, —CN, —COOH, —COCl, —$CONH_2$, —$COR^6$, —CHO, —$SO_2NHR^6$, —$SO_3H$, —$SO_2Cl$ or —$R^5$—$SiR^6{}_c(OR^6)_{3-c}$, $R^5$ represents a divalent hydrocarbon radical having 1 to 8 carbon atoms per radical, $R^6$ is identical or different and represents an alkyl radical having 1 to 8 carbon atoms per radical and c represents 0, 1, 2 or 3, Y is identical or different and represents a ligand selected from the group consisting of Cl, Br, I, $NH_3$, $P(C_2H_5)_3$, $P(C_6H_5)_3$, H, CO, 1,5-cyclooctadiene, pyridine, bipyridine, acetate, acetylacetonate, phenylnitrile, ethylenediamine, acetonitrile, 2,5-norbornadiene, nitrate, nitrite, $H_2O$, benzene, diphenylphosphinoethane and 1,3-divinyl-1,1,3,3-tetramethyldisiloxane, a represents 1, 2, 3 or 4 and b represents 0 or an integer from 1 to 6, with the proviso that platinum-triazenido complexes of the formula $PtZ_2[ANNN(CH_3)]_2$, in which Z represents Cl or I and A has the meaning given above for this symbol, are excluded.

2. A process for the preparation of a complex as claimed in claim 1, which comprises reacting a triazene of the formula

ANNNHR' in which

R' represents a monovalent, optionally substituted hydrocarbon radical having 1 to 18 carbon aroms per radical, excluding aromatic hydrocarbon radicals in which the aromatic part is bonded directly to the nitrogen atom, or a radical of the formula —$SiR^6{}_c(OR^6)_{3-c}$ and A represents a radical of the formula

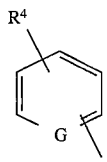

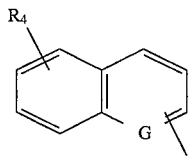

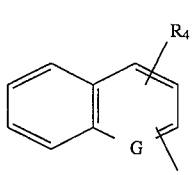

-continued

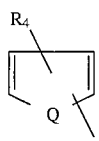

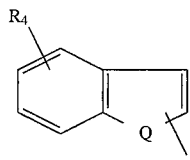

or

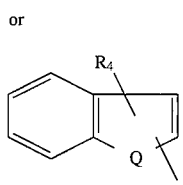

in which

G is CH or N and

Q is S, O or NH, $R^4$ represents a monovalent optionally substituted hydrocarbon radical having 1 to 12 carbon atoms per radical or a radical of the formula —F, —Cl, —Br, —I, —H, —$NH_2$, —$NR^6{}_2$, —$NO_2$, —OH, —$OR^6$, —SH, —CN, —COOH, —COCl, —$CONH_2$, —$COR^6$, —CHO, —$SO_2NHR^6$, —$SO_3H$, —$SO_2Cl$ or —$R^5$—$SiR^6{}_c(OR^6)_{3-c}$, $R^5$ represents a divalent hydrocarbon radical having 1 to 8 carbon atoms per radical, $R^6$ is identical or different and represents an alkyl radical having 1 to 8 carbon atoms per radical and c represents 0, 1, 2 or 3, with transition metal compounds of the formula $M'Y_d$ in which M' represents Pt, Pd, Rh or Ru, Y is identical or different and represents a ligand selected from the group consisting of Cl, Br, I, $NH_3$, $P(C_2H_5)_3$, $P(C_6H_5)_3$, H, CO, 1,5-cyclooctadiene, pyridine, bipyridine, acetate, acetylacetonate, phenylnitrile, ethylenediamine, acetonitrile, 2,5-norbornadiene, nitrate, nitrite, $H_2O$, benzene, diphenylphosphinoethane and 1,3-divinyl-1,1,3,3-tetramethyldisiloxane, and d represents an integer from 1 to 8, in the presence of a base.

3. A crosslinkable organopolysiloxane composition comprising (1) an organopolysiloxane which contains radicals with aliphatic carboncarbon multiple bonds, (2) an organopolysiloxane with Si-bonded hydrogen atoms or, instead of organopolysiloxanes (1) and (2), an organopolysiloxane (3) which contains radicals with aliphatic carbon-carbon multiple bonds and Si-bonded hydrogen atoms and (4) a catalyst of the general formula $MX_aY_b$ (I)

in which

M is Pt, Pd, Rh, Ru, Os or Ir,

X represents a triazene, tetrazene, tetrazadiene or pentazadiene ligand selected from the group consisting of; ANNNR, ANNNRR¹, ANNNA¹, ANR¹NNNR²A¹, ANNNNA¹, ANNNR³NNA¹ and ANNNNNA¹ in which

R represents a monovalent, optionally substituted hydrocarbon radical having 1 to 18 carbon atoms per radical or a radical of the formula —SiR⁶_c(OR⁶)_{3-c}, R¹, R² and R³ are identical or different and represent a hydrogen atom or a monovalent optionally substituted hydrocarbon radical having 1 to 18 carbon atoms per radical, and A and A¹ are identical or different and represent a radical of the formula

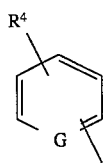

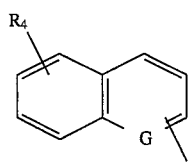

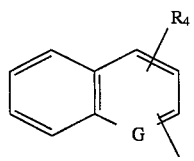

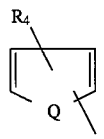

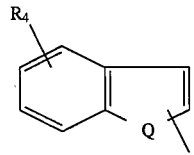

or

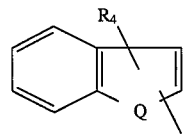

in which

G is CH or N and

O is S, O or NH,

R⁴ represents a monovalent optionally substituted hydrocarbon radical having 1 to 12 carbon atoms per radical or a radical of the formula —F, —Cl, —Br, —I, —H, —NH₂, —NR⁶₂, —NO₂, —OH, —OR⁶, —SH, —CN, —COOH, —COCl, —CONH₂, —COR⁶, —CHO, —SO₂NHR⁶, —SO₃H, —SO₂Cl or —R⁵—SiR⁶_c(OR⁶)_{3-c}, R⁵ represents a divalent hydrocarbon radical having 1 to 8 carbon atoms per radical, R⁶ is identical or different and represents an alkyl radical having 1 to 8 carbon atoms per radical and c represents 0, 1, 2 or 3, Y is identical or different and represents a ligand selected from the group consisting of Cl, Br, I, NH₃, P(C₂H₅)₃, P(C₆H₅)₃, H, CO, 1,5-cyclooctadiene, pyridine, bipyridine, acetate, acetylacetonate, phenylnitrile, ethylenediamine, acetonitrile, 2,5-norbornadiene, nitrate, nitrite, H₂O, benzene, diphenylphosphinoethane and 1,3-divinyl-1,1,3,3-tetramethyldisiloxane, a represents 1, 2, 3 or 4 and b represents 0 or an integer from 1 to 6.

4. A crosslinkable organopolysiloxane composition as claimed in claim 3, wherein the organopolysiloxane is an organopolysiloxane which contains radicals with aliphatic carboncarbon multiple bonds and Si-bonded hydrogen atoms.

5. A process for promoting the addition reaction between an organosilicon compound containing Si-bonded hydrogen atoms and an organic compound containing aliphatic multiple bonds which comprises reacting the organosilicon compound with the organic compound in the presence of a catalyst of the general formula $$MX_aY_b \qquad (I)$$

in which

M is Pt, Pd, Rh, Ru, Os or It,

X represents a triazene, tetrazene, tetrazadiene or pentazadiene ligand selected from the group consisting of; ANNNR, ANNNRR¹, ANNNA¹, ANR¹NNNR²A¹, ANNNNA¹, ANNNR³NNA¹ and ANNNNNA¹ in which

R represents a monovalent, optionally substituted hydrocarbon radical having 1 to 18 carbon atoms per radical or a radical of the formula —SiR⁶_c(OR⁶)_{3-c}, R¹, R² and R³ are identical or different and represent a hydrogen atom or a monovalent optionally substituted hydrocarbon radical having 1 to 18 carbon atoms per radical, and A and A¹ are identical or different and represent a radical of the formula

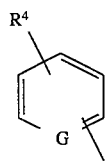

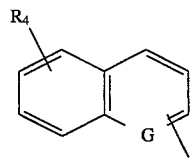

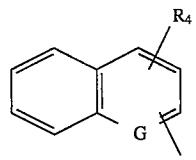

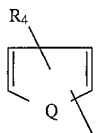

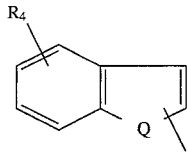

or

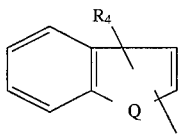

in which

G is CH or N and

Q is S, O or NH, $R^4$ represents a monovalent optionally substituted hydrocarbon radical having 1 to 12 carbon atoms per radical or a radical of the formula —F, —Cl, —Br, —I, —H, —$NH_2$, —$NR^6{}_2$, —$NO_2$, —OH, —$OR^6$, —SH, —CN, —COOH, —COCl, —$CONH_2$, —$COR^6$, —CHO, —$SO_2NHR^6$, —$SO_3H$, —$SO_2Cl$ or —$R^5$—$SiR^6{}_c(OR^6)_{3-c}$, $R^5$ represents a divalent hydrocarbon radical having 1 to 8 carbon atoms per radical, $R^6$ is identical or different and represents an alkyl radical having 1 to 8 carbon atoms per radical and c represents 0, 1, 2 or 3, Y is identical or different and represents a ligand selected from the group consisting of Cl, Br, I, $NH_3$, $P(C_2H_5)_3$, $P(C_6H_5)_3$, H, CO, 1,5-cyclooctadiene, pyridine, bipyridine, acetate, acetylacetonate, phenylnitrile, ethylenediamine, acetonitrile, 2,5-norbornadiene, nitrate, nitrite, $H_2O$, benzene, diphenylphosphinoethane and 1,3-divinyl-1,1,3,3-tetramethyldisiloxane, a represents 1, 2, 3 or 4 and b represents 0 or an integer from 1 to 6, wherein the catalyst is activated by heating at temperatures of 50° C. to 250° C. and/or irradiating with light and/or adding Brönsted acids and/or acid forming agents.

* * * * *